(12) United States Patent
Knoplioch et al.

(10) Patent No.: US 6,975,897 B2
(45) Date of Patent: Dec. 13, 2005

(54) SHORT/LONG AXIS CARDIAC DISPLAY PROTOCOL

(75) Inventors: Jerome Francois Knoplioch, Neuilly sur Seine (FR); DeAnn Haas, Germantown, WI (US); Gilles Roland Moris, Boulogne-Billancourt (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 397 days.

(21) Appl. No.: 10/098,397

(22) Filed: Mar. 15, 2002

(65) Prior Publication Data

US 2002/0156359 A1   Oct. 24, 2002

Related U.S. Application Data

(60) Provisional application No. 60/276,353, filed on Mar. 16, 2001.

(51) Int. Cl.⁷ .................................. A61B 5/05
(52) U.S. Cl. ..................... 600/425; 600/426
(58) Field of Search ................. 600/425, 407, 600/426, 427, 428, 429; 378/21, 22, 23, 24–25; 606/130

(56) References Cited

U.S. PATENT DOCUMENTS

| | | | |
|---|---|---|---|
| 4,259,725 A | | 3/1981 | Andrews et al. |
| 4,858,129 A | | 8/1989 | Mori |
| 4,882,679 A | | 11/1989 | Tuy et al. |
| 5,250,933 A | | 10/1993 | Beaudin et al. |
| 5,371,778 A | | 12/1994 | Yanof et al. |
| 5,590,655 A | * | 1/1997 | Hussman ............... 600/426 |
| 5,722,405 A | | 3/1998 | Goldberg |
| 5,803,914 A | | 9/1998 | Ryals et al. |
| 6,141,398 A | | 10/2000 | He et al. |
| 6,249,693 B1 | * | 6/2001 | Cline et al. ............ 600/410 |
| 6,275,035 B1 | | 8/2001 | Debbins et al. |
| 6,438,403 B1 | * | 8/2002 | Cline et al. ............ 600/410 |
| 6,470,207 B1 | * | 10/2002 | Simon et al. ........... 600/426 |
| 6,484,049 B1 | * | 11/2002 | Seeley et al. .......... 600/426 |
| 6,490,475 B1 | * | 12/2002 | Seeley et al. .......... 600/426 |
| 6,567,687 B2 | * | 5/2003 | Front et al. ............ 600/426 |
| 6,724,922 B1 | * | 4/2004 | Vilsmeier ............... 382/128 |

\* cited by examiner

*Primary Examiner*—Daniel Robinson
(74) *Attorney, Agent, or Firm*—Carl B. Horton, Esq.; Armstrong Teasdale LLP (57) ABSTRACT

A method for generating views of a heart along anatomically useful planes includes generating a prescription image of a heart, receiving data regarding a position of at least one landmark on the prescription image to define a series of slices through the heart along at least one anatomical plane lane, generating a plurality of images under software control, and saving the generated images.

5 Claims, 13 Drawing Sheets

Screen layout once the data sets are loaded:

| Oblique | Sagital w/ line |
|---|---|
| Protocol Box | Axial |

To define the short/long axis views of the heart:

Page through the sagital image and find the image with the mitral valve and apex of the heart. Rotate the yellow line so it goes through the mitral valve and apex.

Select next to bring up the batch lines to produce the 4 chamber long axis views.

[ Close ]          [ Next ]

An oblique line should be placed on the sagital view.

Detailed view of the protocol box (Magnify the image to see the prescription lines).

Figure 14 ially referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

SHORT/LONG AXIS CARDIAC DISPLAY PROTOCOL

CROSS REFERENCE TO RELATED APPLICATIONS

This application claims the benefit of U.S. provisional application No. 60/276,353 filed Mar. 16, 2001.

BACKGROUND OF THE INVENTION

This invention relates generally to CT and MR examinations of the heart, and more specifically to methods and apparatus for producing a long/short axis protocol from prescription images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object includes a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

CT and MR (magnetic resonance) examinations now allow non-invasive imaging of the heart. They provide 3D data from which medical analysis or surgical planning may be performed. Image quality is quickly improving and 3D x-ray acquisitions may also soon provide the same information.

The most natural acquisition method (the only one in the case of CT) is along axial slices that do not correspond to a specific orientation of the heart, but just to horizontal planes. Displaying the heart along slices that contain its long or short axis is of great interest for assessing heart function. Such displays may be used to show the valves and the ventricles or to quantify the volume of the ventricles at different phases along the cardiac cycle. Acquiring MR slices in planes containing its long or short axis is a commonly used method, but requires an operator to have knowledge of cardiac anatomy and increases prescription time. In the case of CT, displaying slices in these planes has been done by post-processing of acquired CT data, because known CT scanners are capable only of acquiring data representative of axial slices.

It would therefore be desirable to provide methods and apparatus to facilitate the creation of a volume of slices along a short or long axis of the heart. It would also be desirable to make such methods readily accessible to untrained operators.

BRIEF SUMMARY OF THE INVENTION

In one aspect, a method for generating views of a heart along anatomically useful planes is provided. The method includes generating a prescription image of a heart, receiving data regarding a position of at least one landmark on the prescription image to define a series of slices through the heart along at least one anatomical plane lane, generating a plurality of images under software control, and saving the generated images.

In another aspect, a computer readable medium encoded with a program executable by a computer for generating views of a heart along anatomically useful planes is provided. The program is configured to instruct the computer to generate a prescription image of a heart, receive data regarding a position of at least one landmark on the prescription image to define a series of slices through the heart along at least one anatomical plane, generate a plurality of images, and save the generated images.

In a further aspect, a medical imaging for generating views of a heart along anatomically useful planes is provided. The medical imaging system includes a detector array, at least one radiation source, and a computer coupled to said detector array and radiation source and configured to generate a prescription image of a heart, receive data regarding a position of at least one landmark on the prescription image to define a series of slices through the heart along at least one anatomical plane, generate a plurality of images, and save the generated images.

DETAILED DESCRIPTION OF THE INVENTION

Figure 1:
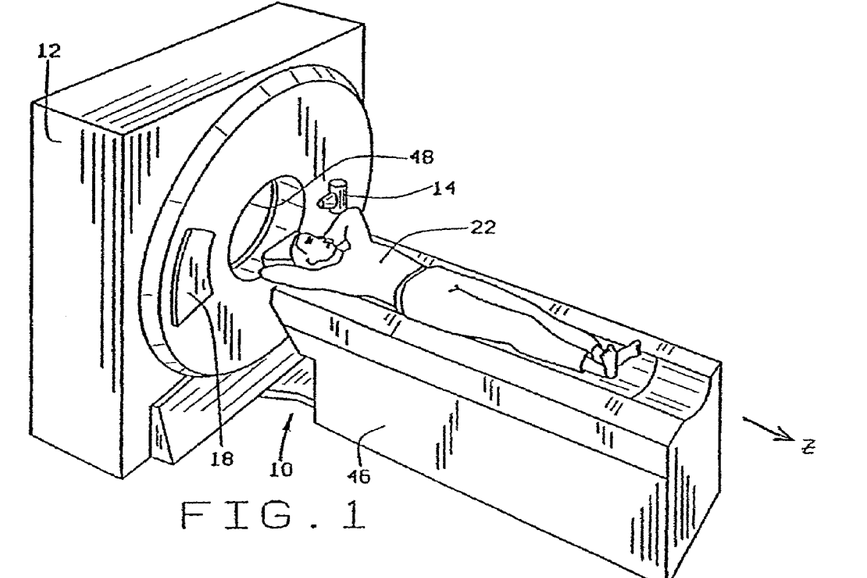
FIG. 1 is a pictorial view of a CT imaging system.
Figure 2:
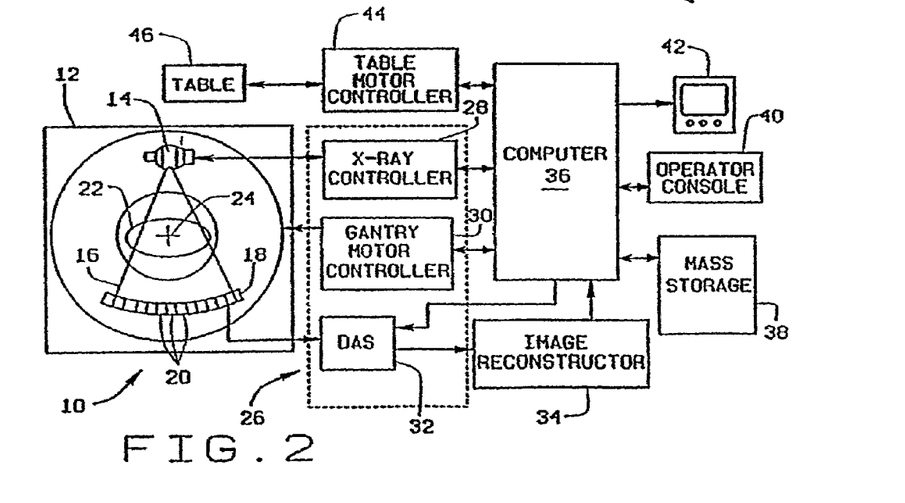
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has a x-ray source 14 that projects a beam of x-rays 16 toward a radiation detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam on that detector element and hence the attenuation of the beam as it passes through patient 22 at a corresponding angle. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device (not shown), for example, a floppy disk drive or CD-ROM drive, for reading instructions and/or data from a computer-readable medium (not shown), such as a floppy disk or CD-ROM. In another embodiment, computer 36 executes instructions stored in firmware (not shown). Computer 36 is programmed to perform functions described herein, but other programmable circuits can be likewise programmed. For example, in one embodiment, DAS 32 performs functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

In one embodiment of the present invention, a user of CT system 10 selects an exam (i.e., a prescription image) containing a volume data set that represents the heart at a given phase, or multiple volume data sets that represent the heart at multiple phases. A software program running in computer 36 is then launched by the operator using display 42 and console 40. This software accepts as inputs designations of the volume data sets selected by the user. In use, the user selects a short/long axis protocol and a user interface then appears on display 42. The short/long axis protocol is used to define a short axis, a horizontal long axis, and a vertical long axis. The protocol is a multiple protocol that steps the user through each phase. The user has the ability to skip any view for which an image is not desired. In one embodiment, the user interface is a step-by-step guide to allow the user to produce the short/long axis view.

Figure 3:
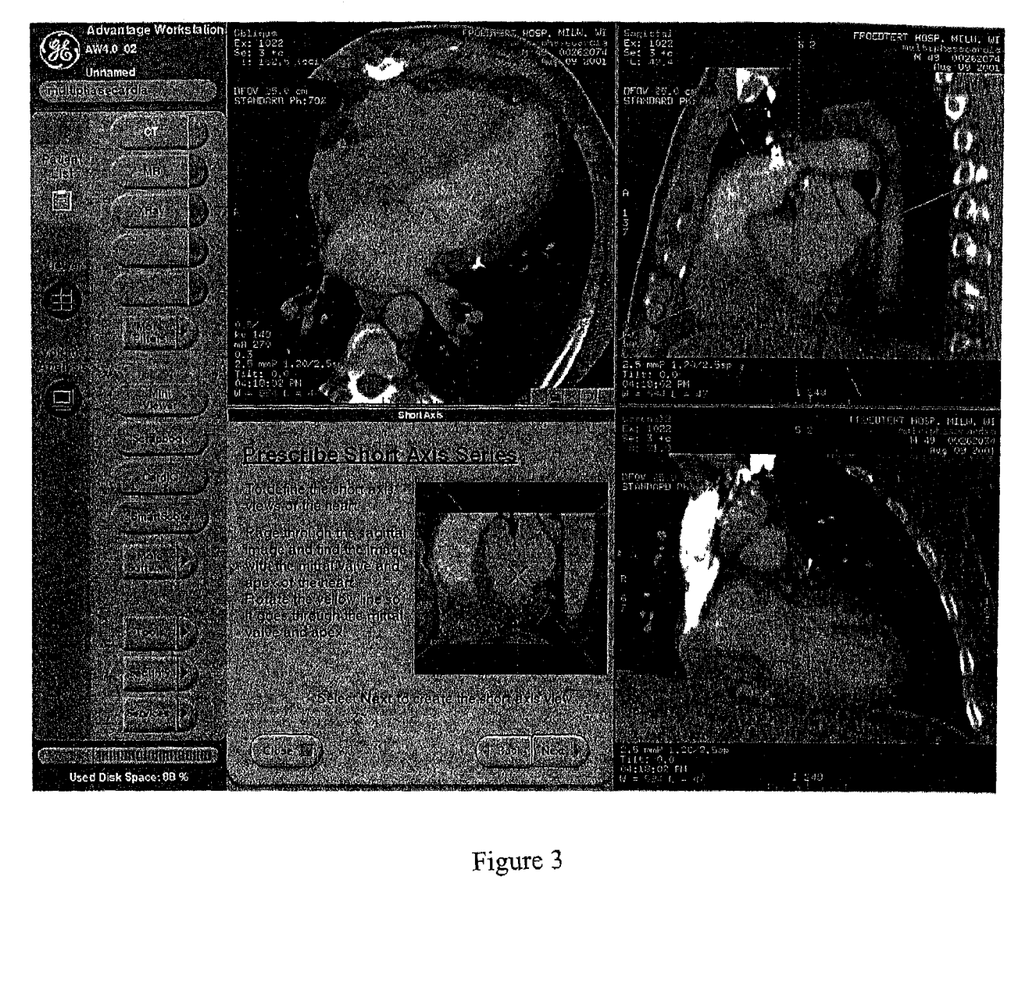
FIG. 3 is an exemplary embodiment of a user interface of a CT imaging system displaying a first page of a short/long axis protocol.
Figure 4:
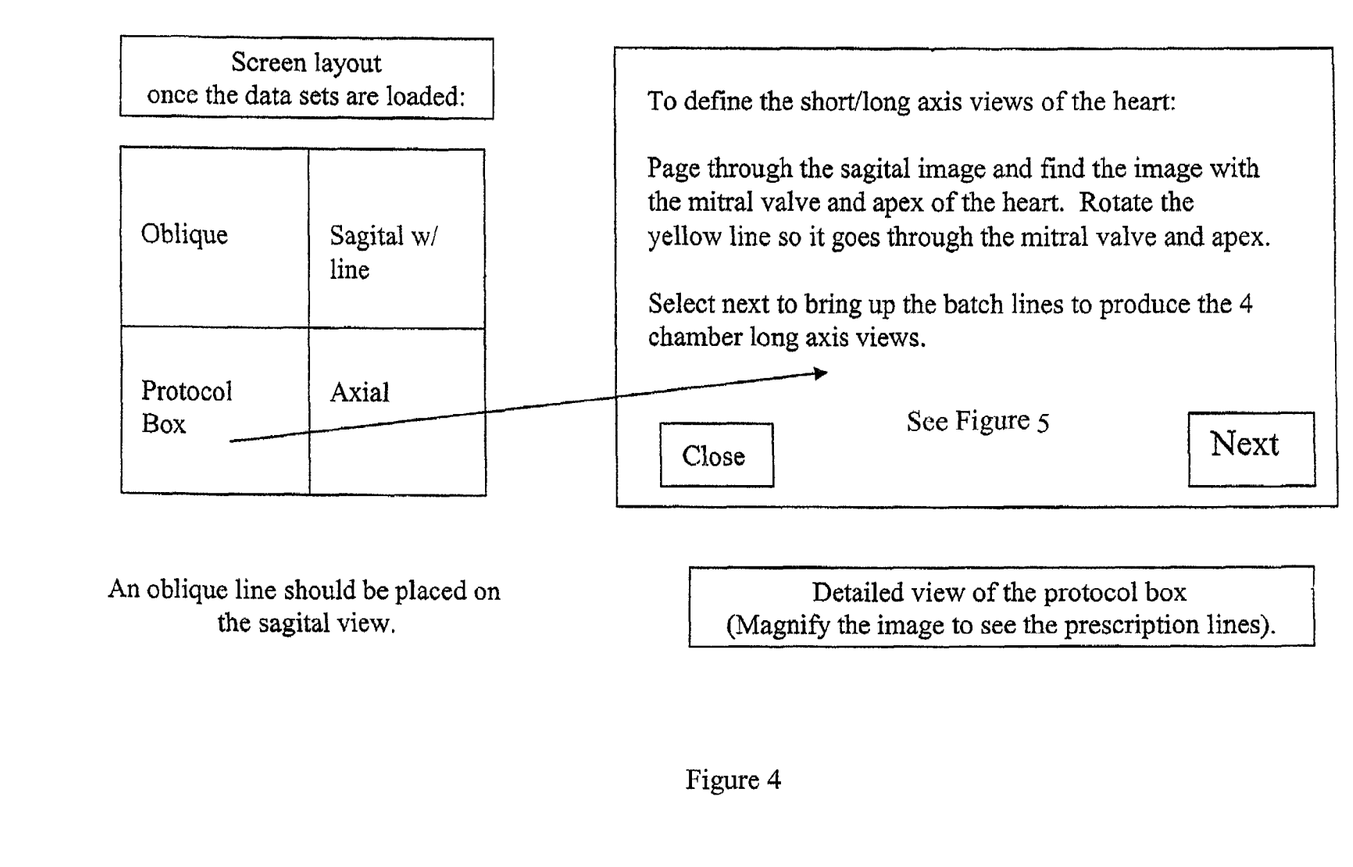
FIG. 4 is a schematic illustration of the user interface shown in FIG. 3.
Figure 5:
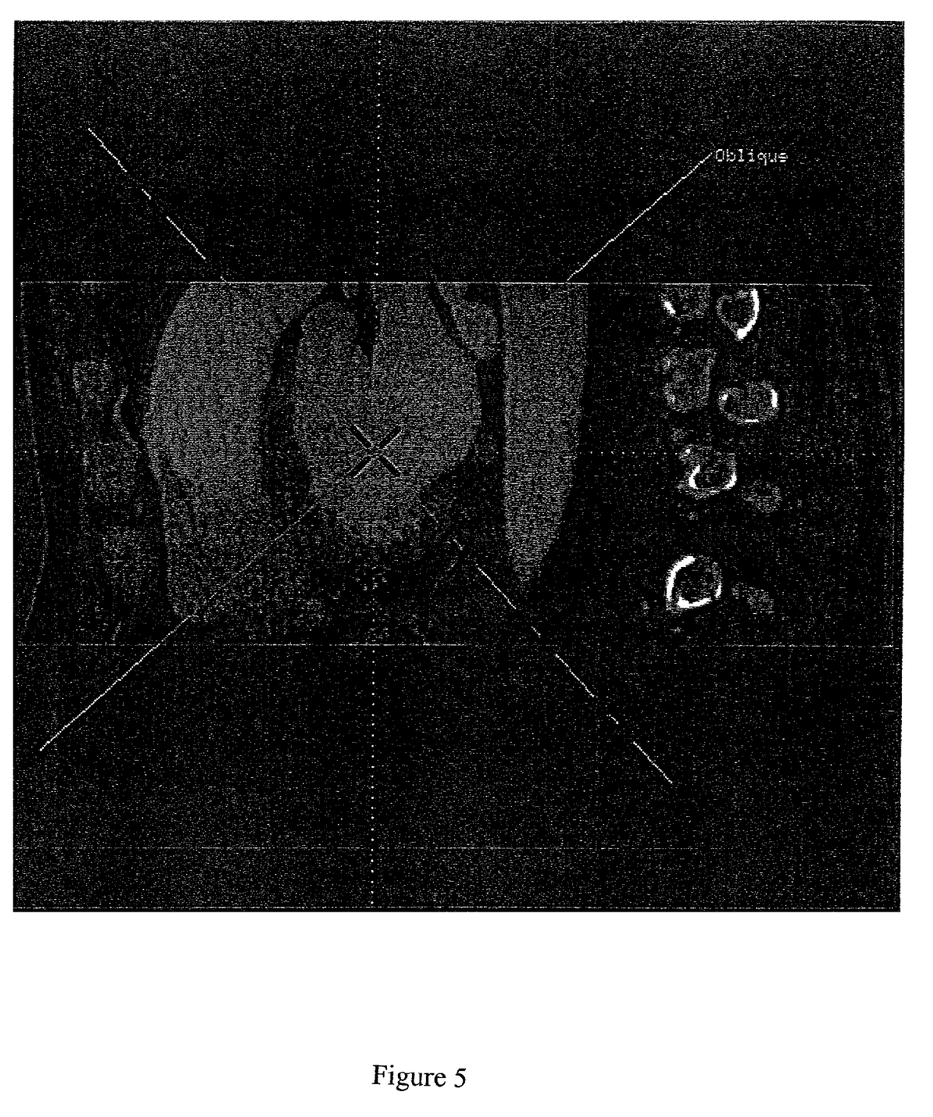
FIG. 5 is a sagittal view of a heart.

FIG. 3 is an exemplary embodiment of a user interface of a CT imaging system displaying a first screen (shown in FIG. 1) after the user selects the short/long axis protocol. FIG. 4 is a schematic illustration of the user interface shown in FIG. 3. In exemplary embodiment, the user interface displayed on display 40 includes a protocol box and a plurality of views of the heart, such as an oblique long axis view including lines, a sagittal view including batch lines, and an axial view. The protocol box provides instructions for defining the short/long views of the heart. The protocol instructions include, but are not limited to, paging through the sagittal image to find an image with a mitral valve and apex of the heart, rotating a yellow line so that it joins these features. The user then selects "next" to bring up a plurality of batch lines to produce at least one 4-chamber long axis view as shown in FIG. 5. Alternatively, the user can select "close" to end the program.

Figure 6:
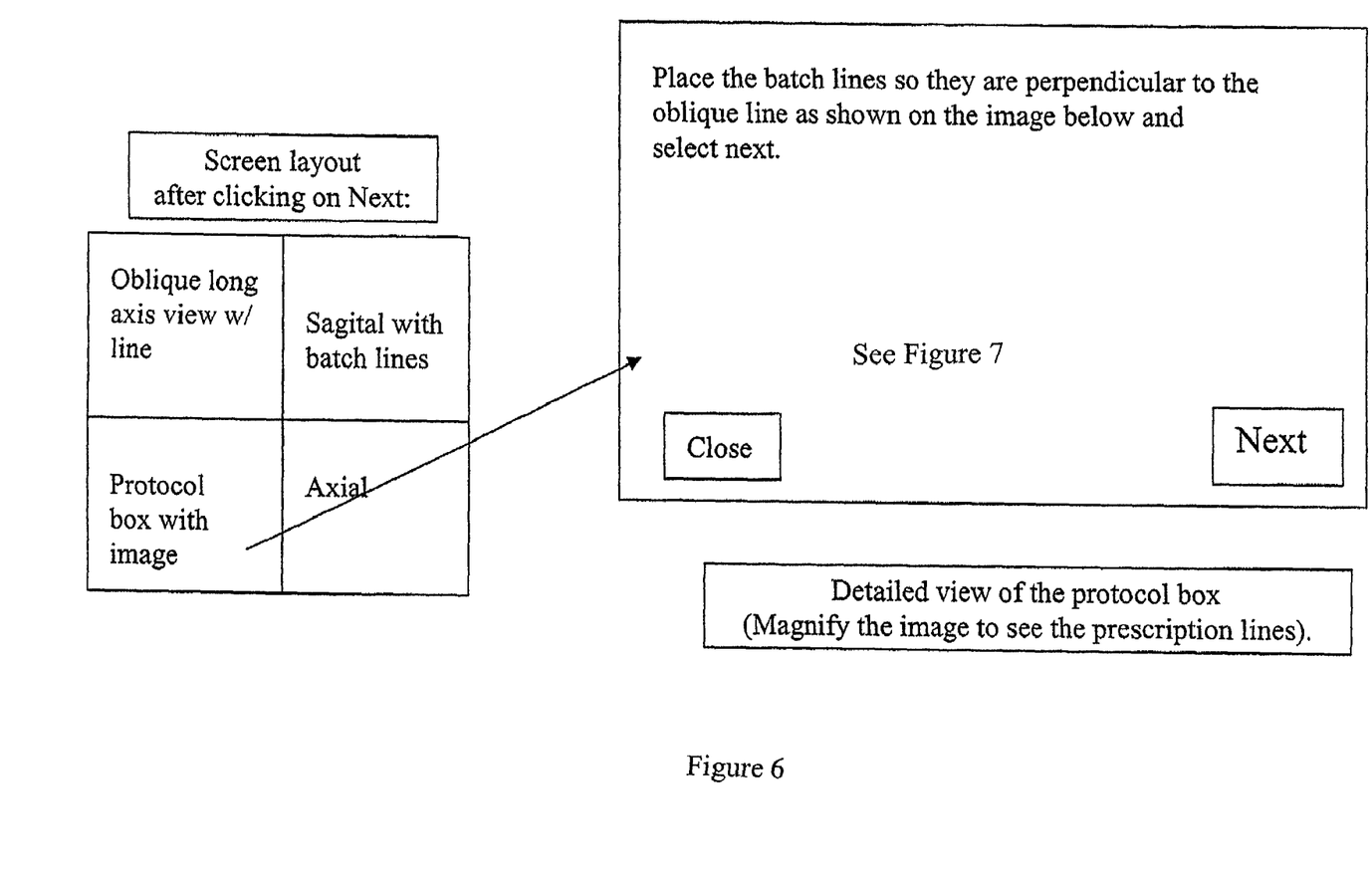
FIG. 6 is an example embodiment of a user interface of a CT imaging system displaying a second page of a short/long axis protocol.
Figure 7:
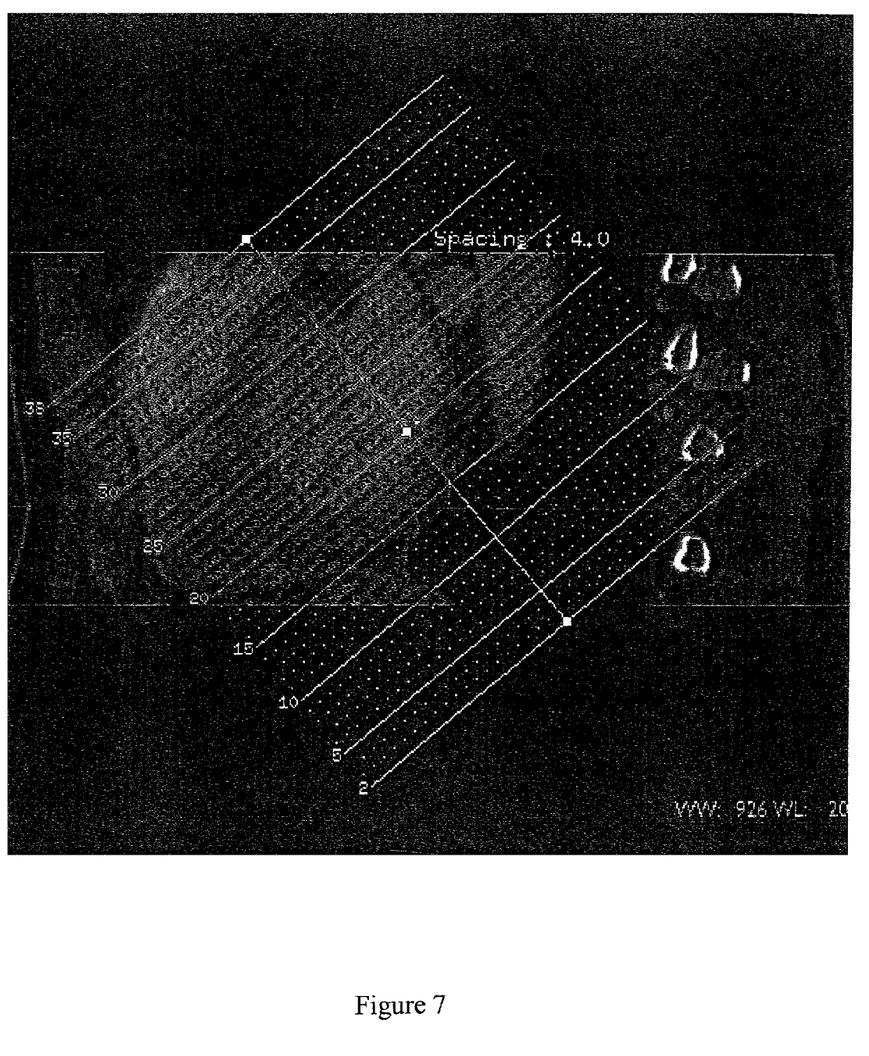
FIG. 7 is an image of the heart showing placement of batch lines placed perpendicular to an oblique line on an image of the heart.

FIG. 6 is an example embodiment of a user interface that illustrates a second screen that is displayed on display 42. At this point, computer 36 processes and displays batch protocol lines on a sagittal image displayed on display 42. A double oblique image line also appears and stays on the image. Using display 42 and console 40 under control of computer 36, the user places a plurality of batch lines so the batch lines are perpendicular to the oblique line as shown in FIG. 7. The user then selects "next". Alternatively, the user can select "close" to end the program.

Figure 8:
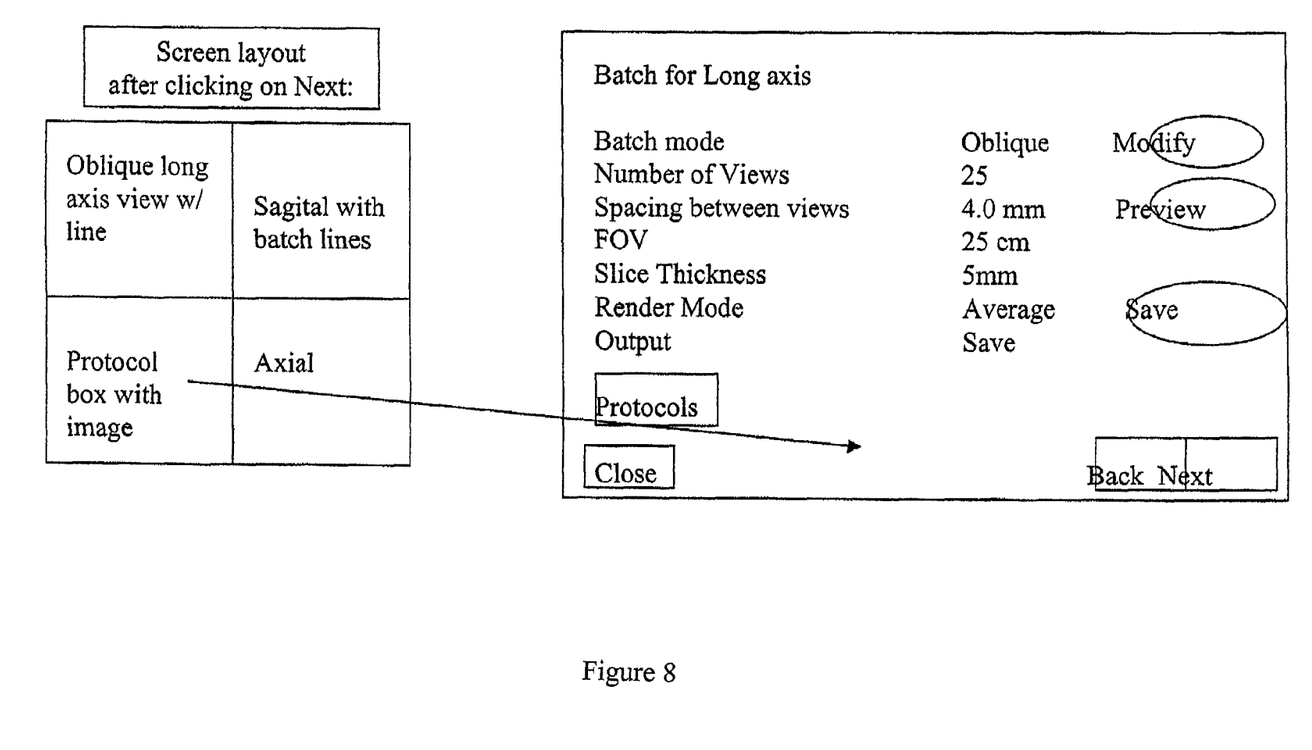
FIG. 8 is an example embodiment of a user interface of a CT imaging system displaying a third page of a short/long axis protocol.

FIG. 8 is an example embodiment of a user interface that illustrates a third screen that is displayed on display 42. Next, the user requests software in computer 36 to modify or save the 4-chamber views. To instruct computer 36 to modify the views, the user clicks on a displayed "modify" button, which causes the software to display a batch modify screen. From here, the user can instruct the software to change the number of views, the spacing between views, the field of view (FOV), or slice thickness. Users are also able to instruct software in computer 36 to perform other CT imaging processing functions in the modify batch screen. If the protocol is acceptable, the user is presented with the option of saving the images. In one embodiment, there is a "back" button on the screen to allow the user to specify a different position of the sagittal view line, and a "next" button to allow the user to instruct the software in computer 36 to produce short axis images. If multiphase data are loaded, the saved results may also be multiphase in one embodiment. After "next" is selected, batch lines will appear on a long axis view. The batch lines are perpendicular to the long axis, so that they cover the base to apex of the heart as shown in FIG. 7.

Figure 9:
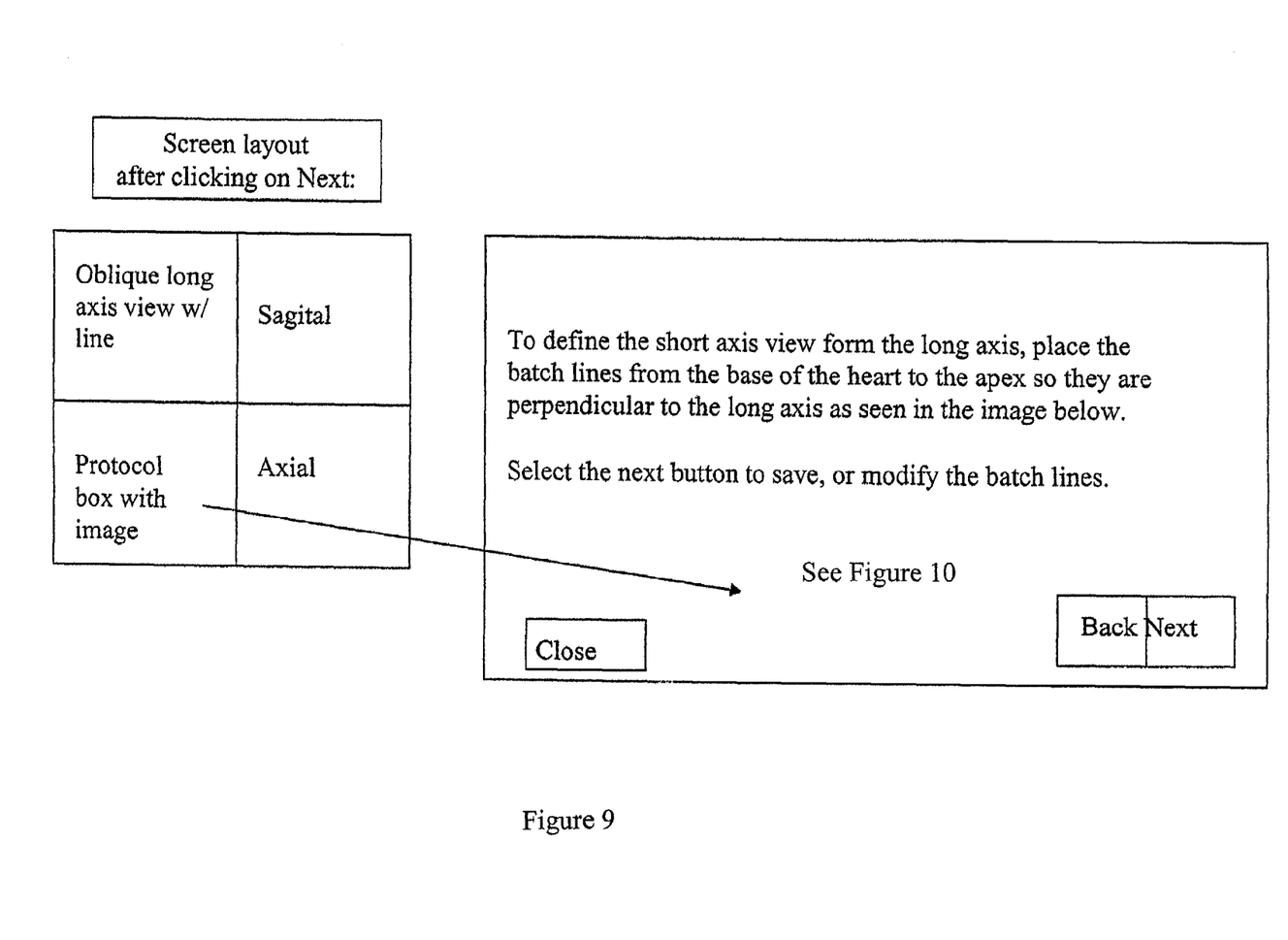
FIG. 9 is an example embodiment of a user interface of a CT imaging system displaying a fourth page of a short/long axis protocol.
Figure 10:
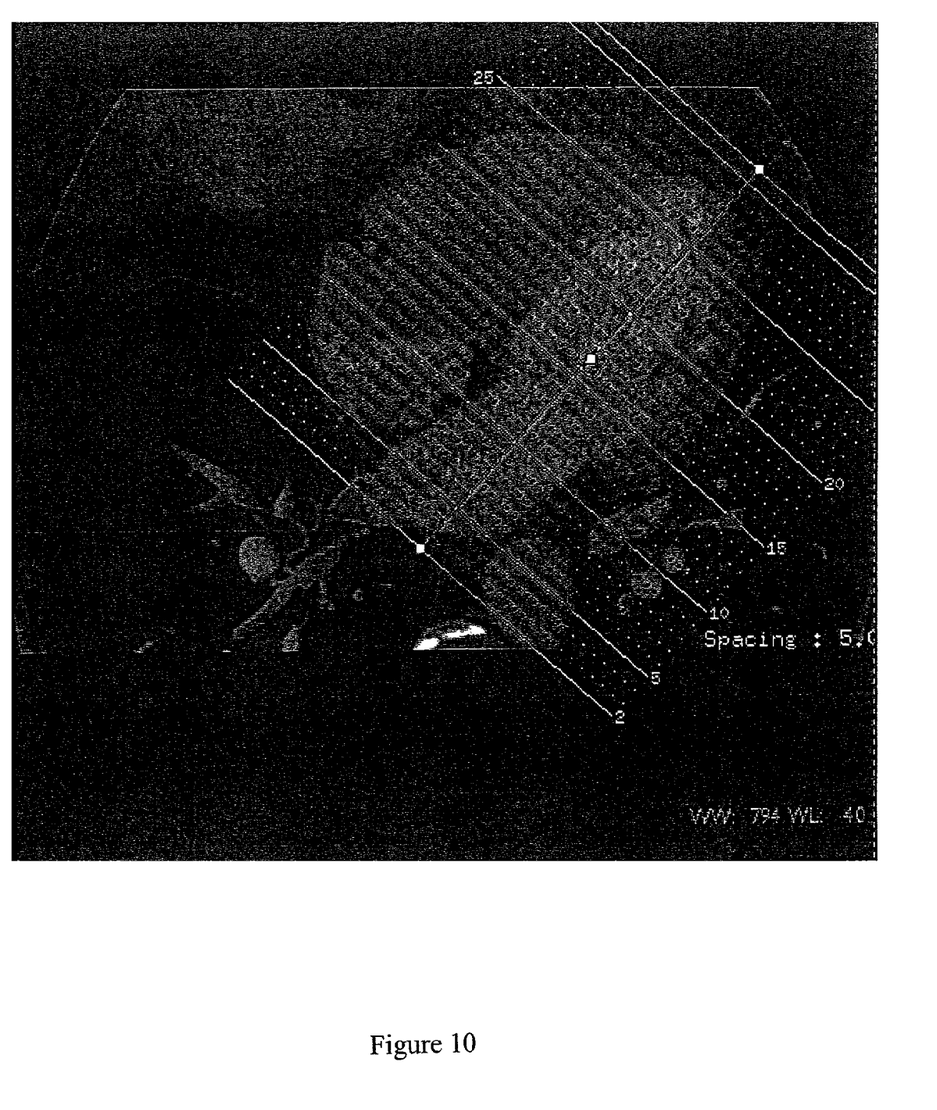
FIG. 10 is an image of the heart showing a definition of a short axis view from a long axis view.

FIG. 9 is an example embodiment of a user interface that illustrates a fourth screen that is displayed on display 42. Next, the user can instruct the software to present a view shown in FIG. 10 of the short axis in one portion of display 42, for example, the upper right portion. The user then selects a "next" button or a "back" button. If the "back" button is selected, the software returns to a point at which the first page of instructions is displayed. If "next" is selected, the user is presented with options to modify, preview or save short axis views as shown in FIG. 11.

Figure 11:
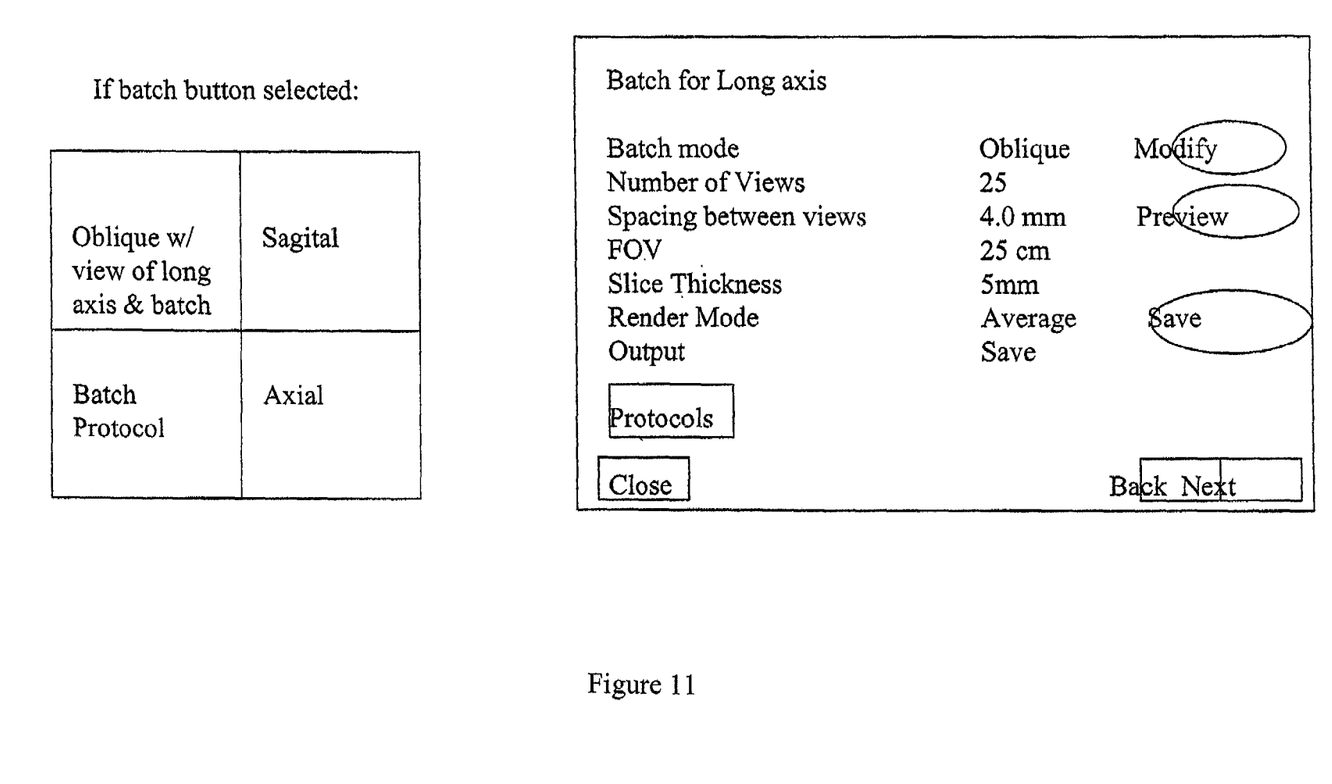
FIG. 11 is an example embodiment of a user interface of a CT imaging system displaying a fifth page of a short/long axis protocol.

FIG. 11 is an example embodiment of a user interface that illustrates a fifth screen that is displayed on display 42. To modify the short axis views, the user clicks on a "modify" button so that the software presents a batch modify screen on display 42. The batch screen presents the user with options that change the number of views, spacing between the views, field of view (FOV), slice thickness, render mode, and output. If the protocol is acceptable, the user is provided with options for saving the images. In one embodiment, a "back" button is provided to allow the user to go back to a screen in which the position of the sagittal view line can be changed. In addition, a "next" button is provided to advance the display to a 2 chamber long axis view.

Figure 12:
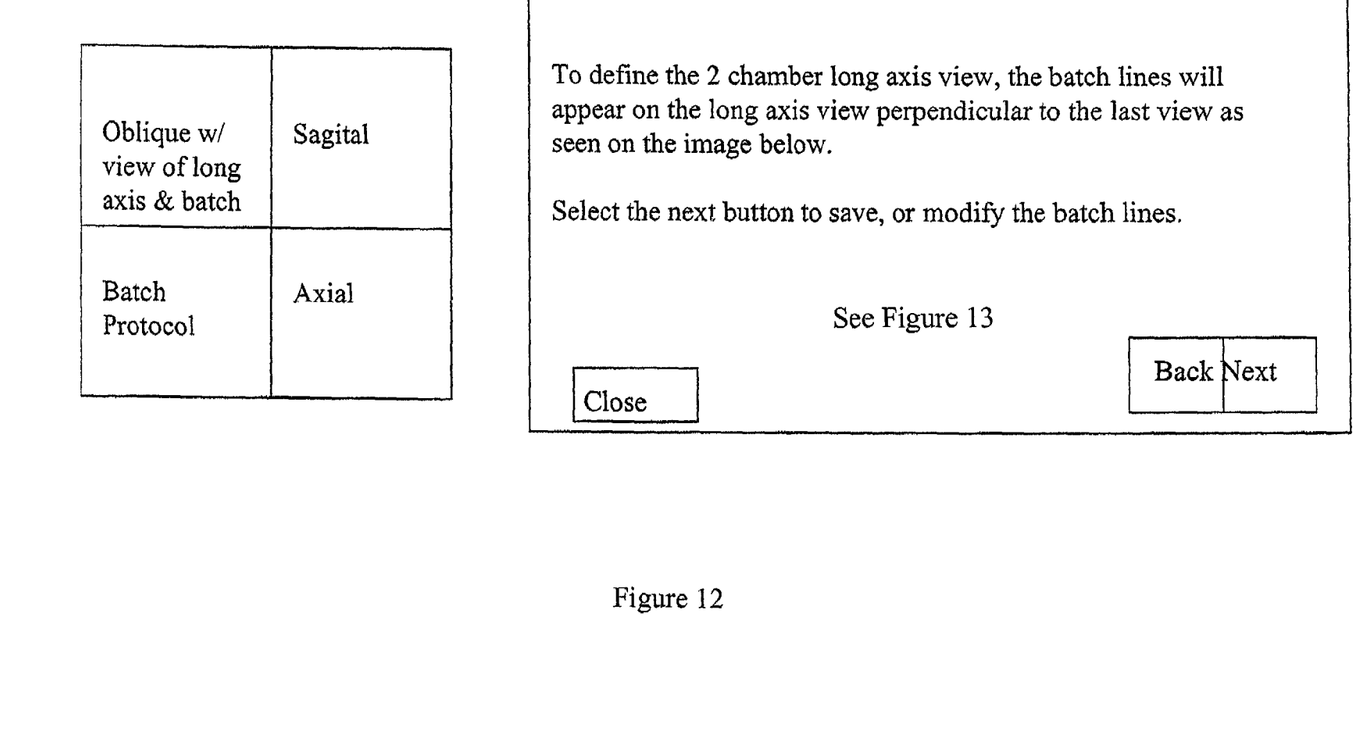
FIG. 12 is an example embodiment of a user interface of a CT imaging system displaying a sixth page of a short/long axis protocol.
Figure 13:
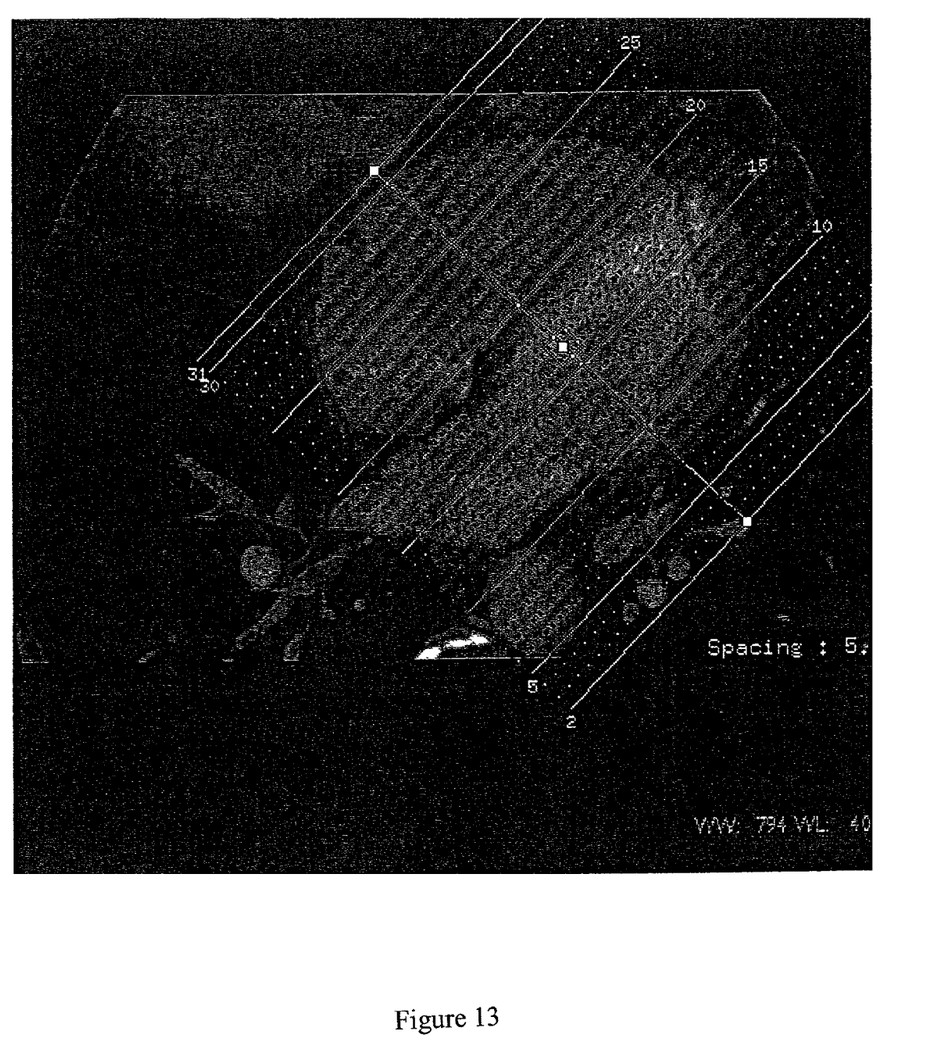
FIG. 13 is an image of the heart showing a definition of a 2 chamber long axis view.

FIG. 12 is an example embodiment of a user interface that illustrates a sixth screen that is displayed on display 42. When the "next" button is selected in FIG. 12, the user batch protocol lines are rotated so that they are perpendicular to their previous position, so that a 2 chamber long axis view is produced by computer 36 for display on display 42 as shown in FIG. 13. The user is then presented with options to modify or save the 2 chamber long axis views. To modify or save the views, the user clicks a "next" button to cause the software running in computer 36 to display a batch modify screen on display 42. Alternatively, the user can select "close" to end the program.

Figure 14:
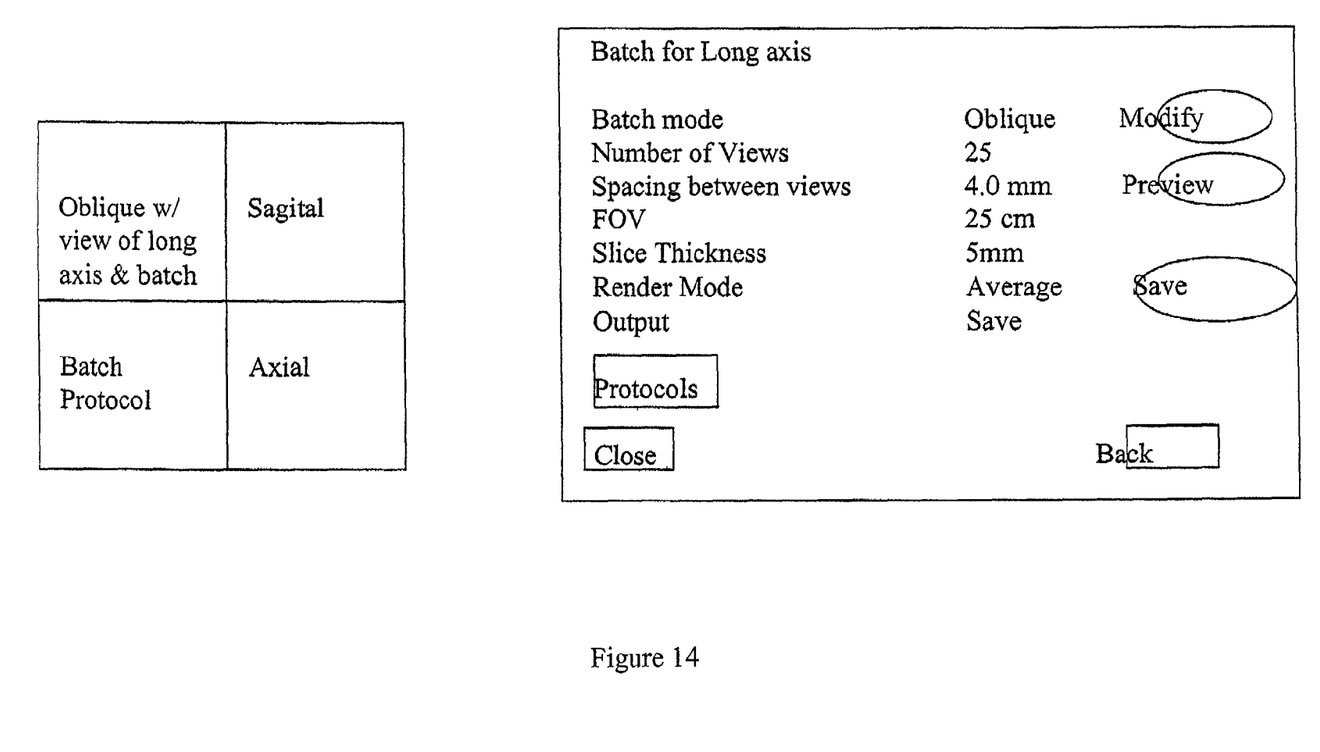
FIG. 14 is an example embodiment of a user interface of a CT imaging system displaying a seventh page of a short/long axis protocol.

FIG. 14 is an example embodiment of a user interface that illustrates a seventh screen that is displayed on display 42. When the "next" button is selected in FIG. 10, the user batch protocol presents options for the user to change the number of views, spacing between the views, field of view (FOV), slice thickness, render mode, and output. The user can also instruct the software to perform other functions provided by the "modify batch" screen. If the protocol selected is acceptable, the user is presented with options for saving the images. In one embodiment, a "back" button is provided to allow the user to change the position of the sagittal view line. Alternatively, the user can select "close" to end the program.

In each case, where "save" is selected, the software provides the user with an option to save to any of various archival media, including film and computer media. Thus, in one embodiment of the present invention, a method is provided for generating views of the heart along anatomically useful planes, wherein the method includes generating a prescription image of the heart, and using a computer and display (for example, computer 36 and display 42) to prompt and assist a user with visual aids, such as exemplary images and text, to position landmarks. As used herein, landmarks refers to anatomical structures, such as, but not limited to, an apex of the heart, selected by the operator to facilitate positioning the batchlines to define a series of slices through the heart along known anatomical planes. The computer then generates the images under software control and displays and/or saves the images. In one embodiment, the images are saved without further operator intervention. Also in one embodiment, the images are saved to an archival film. In another embodiment, the images are saved to a computer media, such as a floppy disk, tape, or hard drive.

In another embodiment, a method is provided to generate views of the heart along anatomically useful planes. The method includes generating a prescription image of the heart and using a computer and display to prompt a user to position landmarks on a prescription image to define a series of slices through a heart along known anatomical planes. The computer then generates the images under software control and displays and/or saves the images. In one embodiment, the images are saved without further operator intervention. Also in one embodiment, the images are saved to an archival film. In another embodiment, the images are saved to a computer media, such as a floppy disk, tape, or hard drive.

In yet another embodiment, views of the heart are generated along anatomically useful planes by a method that includes generating a prescription image of the heart and using a computer and a display to prompt and assist a user with visual aids to position landmarks on a prescription image so that a series of slices through a heart along known anatomical planes is defined. The series is then used by the computer to generate images. The images are saved by the computer to archival media without further user intervention. The computer then obtains a new orientation defined by the user to obtain a new prescription image. The computer and display are then used again to prompt and assist the user to position landmarks, and another series of images is saved by the computer.

In still another embodiment of the present invention, views of the heart along anatomically useful planes are generated by a method that includes generating a prescription image of the heart and using a computer to prompt and assist a user with visual aids to position landmarks on a prescription image so that a series of slices through a heart along known anatomical planes is defined. The series is used by the computer to generate images, which are then saved by the computer to archival medial without further user intervention. The computer uses an orientation defined by the user to compute a new prescription image, and the computer and display are used to prompt the user to position landmarks for further image generation and saving.

In some embodiments, user intervention is accepted for the saving of images. For example, in one embodiment, the user is prompted to specify a type of media or the file location(s) for saving the series of images. In another embodiment, the user is given the opportunity to exit the program, to return to a previous step (for example, to correct an error) or to continue without saving the images.

It will be seen that embodiments of the present invention visually guide an operator through a series of steps so that his or her prescription will be accurate even without training. In the case of CT imaging, embodiments of the present invention allow a user to create a full four-dimensional (4D) data set that is well-suited to functional study of the heart and that can be used in conjunction with analysis software applications. In one embodiment, the 4D data set includes a three-dimensional image and a time component.

In addition, embodiments of the present invention are able to load CT images in a single phase of the heart or multiple phases at the same location. For example, a single phase data set can include image location S0 to I100 at 70% of the R to R interval. A multiphase data set might include image locations S0 to I100 at ten phases from 0 to 100% of the R to R interval. Data sets in one embodiment of the present invention have the same short/long axis plane throughout, thereby allowing a user to observe wall motion, ejection fracture, wall thickness, and perfusion.

In MR applications, post-processing embodiments of the present invention may be used to create short and long axis views. One post-processing embodiment of the present invention utilizes data obtained from MR, but utilizes software running on a computer separate from the MR as well as a separate display and operator console. This embodiment reduces the scan prescription time. Cost is also reduced, because time on the operator console is more expensive than time at a workstation. Thus, clinical productivity (measured in MR patients scanned per day) is increased by this embodiment. In addition, embodiments of the present invention allow rescans to be avoided if prescriptions are not correct.

While the invention has been described in terms of various specific embodiments, those skilled in the art will recognize that the invention can be practiced with modification within the spirit and scope of the claims.

What is claimed is:

1. A method for generating views of a heart along anatomically useful planes, comprising:
   generating a prescription image of a heart;
   receiving data regarding a position of at least one landmark on the prescription image to define a series of slices through the heart along at least one anatomical plane;
   generating a plurality of images;
   saving the generated images; and
   selecting a short/long axis protocol.

2. A method in accordance with claim 1 wherein said generating a prescription image of a heart further comprises loading at least one a volume data set that represents a heart at a desired phase and a plurality of volume data sets of the heart at a plurality of desired phases in the computer.

3. A method in accordance with claim 1 wherein said receiving data regarding a position of at least one landmark on the prescription image further comprises assisting a user with a plurality of visual aids to position the landmarks on the prescription image.

4. A method in accordance with claim 3 wherein said assisting a user with visual aids to position the landmarks further comprises assisting a user with at least one of an example image and a detailed text to position the landmarks.

5. A method in accordance with claim 1 wherein said generating a plurality of images under software control further comprises generating a plurality of 4D images under software control.

* * * * *